United States Patent [19]
Lo et al.

[11] Patent Number: 5,275,607
[45] Date of Patent: Jan. 4, 1994

[54] INTRAOCULAR SURGICAL SCISSORS

[75] Inventors: Thomas Y. Lo; Franklin Tao, both of Fremont; Tolentino Escorcio, San Leandro, all of Calif.; Kirk H. Packo, Flossmoor, Ill.

[73] Assignee: Visionary Medical, Inc., Fremont, Calif.

[21] Appl. No.: 764,518

[22] Filed: Sep. 23, 1991

[51] Int. Cl.$^5$ .............................. A61B 17/32
[52] U.S. Cl. ..................... 606/169; 604/22; 606/170; 606/174; 606/39
[58] Field of Search ............... 606/166, 167, 168, 169, 606/170, 171, 174, 177, 178, 179, 180, 39; 604/22; 128/751, 755

[56] References Cited
U.S. PATENT DOCUMENTS

| | | | |
|---|---|---|---|
| 3,832,776 | 9/1974 | Sawyer | 30/272.1 |
| 3,899,829 | 8/1975 | Storm et al. | 30/228 |
| 4,200,106 | 4/1980 | Douvas et al. | 606/168 |
| 4,210,146 | 7/1980 | Banko | 606/171 |
| 4,428,748 | 1/1984 | Peyman et al. | 604/22 |
| 4,877,026 | 10/1989 | de Laforcade | 606/171 |
| 4,898,575 | 2/1990 | Fischell et al. | 604/22 |
| 4,911,161 | 3/1990 | Schechter | 606/107 |
| 5,085,662 | 2/1992 | Willard | 606/159 |
| 5,087,265 | 2/1992 | Summers | 606/159 |

FOREIGN PATENT DOCUMENTS 0835436 6/1981 U.S.S.R. ............... 606/169

OTHER PUBLICATIONS

2-Page Sales Brochure by Grieshaber & Co. Inc., undated, "The Proportional Control System".
4-Page Sales Brochure distributed by Grieshaber & Co. Inc., undated, "MPC Membrane Peeler Cutter".
4-Page Sales Brochure distributed by Grieshaber & Company, Fallsington, Pa., undated, "The Membrane Peeler Cutter".
5-Page Sales Brochure by Grieshaber & Co. Inc., undated, "Sutherland rotatable Intraocular Microscissors".
2-Page Sales Brochure by Alcon Surgical Inc., 1991, on "New Disposable Microscissors".
5-Page Sales Brochure by DORC, Holland, "Microsurgical System for Anterior and Posterior Segment Surgery", undated.
1-Page Sales Brochure by Grieshaber & Co. Inc., undated, "Oscillating Knife".
1-Page Sales Brochure by Storz Instrument Company, undated, "The Smooth Removers".
3-Page Sales Brochure by Trek, undated, "Automated Scissors Drive".
2-Page Sales Brochure by Trek, undated, "Glaucoma Mechanical Trephine".
Arch Ophthalmol-vol. 99, Jan. 1991 2 pgs. article: "Membrane Peeler Cutter-Automated Scissors and Hooked Needle", by Machemer, Parel, Hickingbotham, and Nose.

Primary Examiner—Edgar S. Burr
Assistant Examiner—Christopher A. Bennett
Attorney, Agent, or Firm—Fitch, Even, Tabin & Flannery

[57] ABSTRACT

An intraocular scissors including a handpiece which supports a detachable assembly having a pair of elongated relatively reciprocable blade members suitable for intraocular surgery. One of the blade members is fixedly mounted with respect to the handpiece and the other is mounted for reciprocating movement. Drive means are provided to operate the scissors in various modes including different rates of movement of the reciprocating blade member.

22 Claims, 13 Drawing Sheets

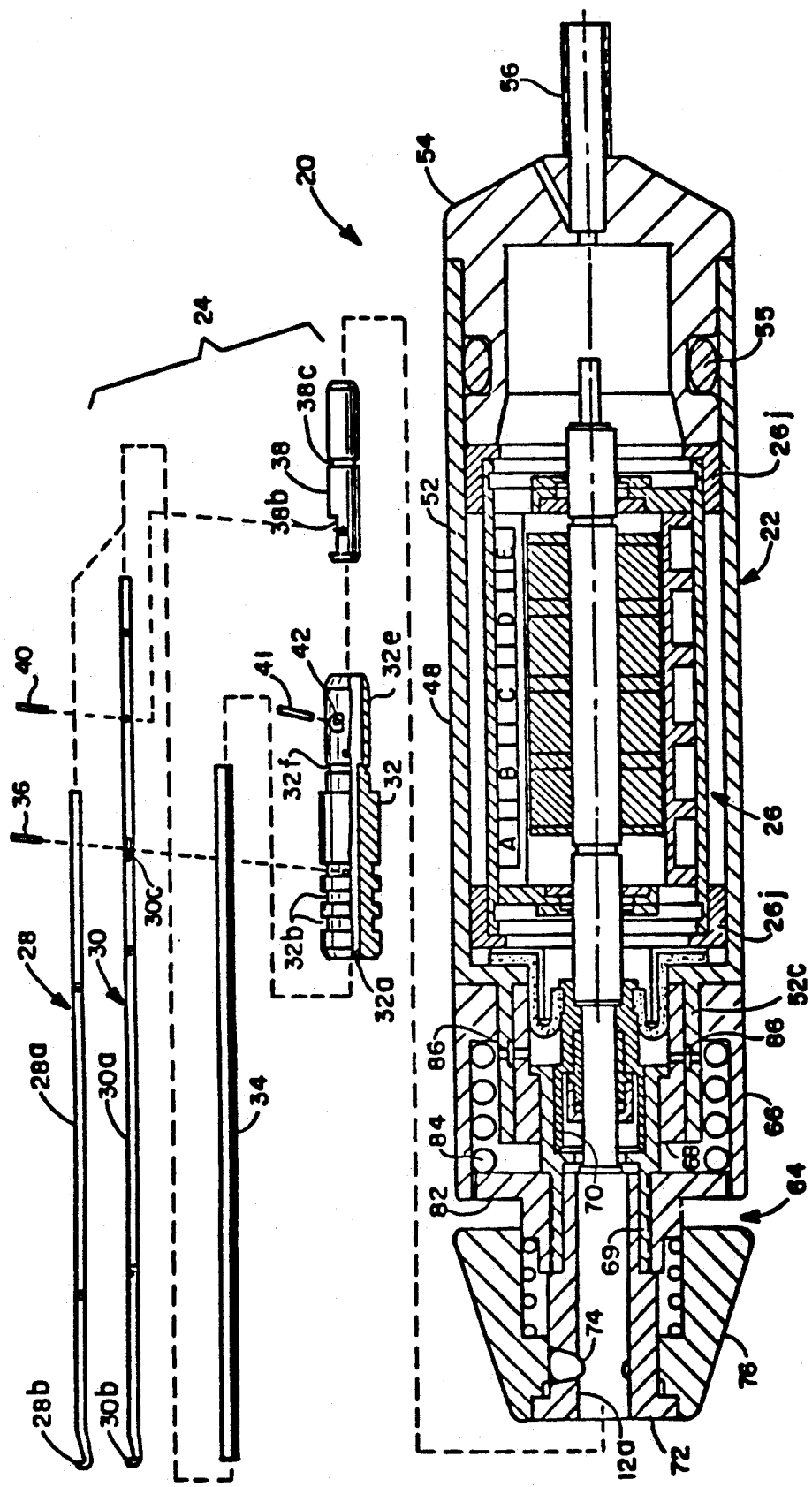

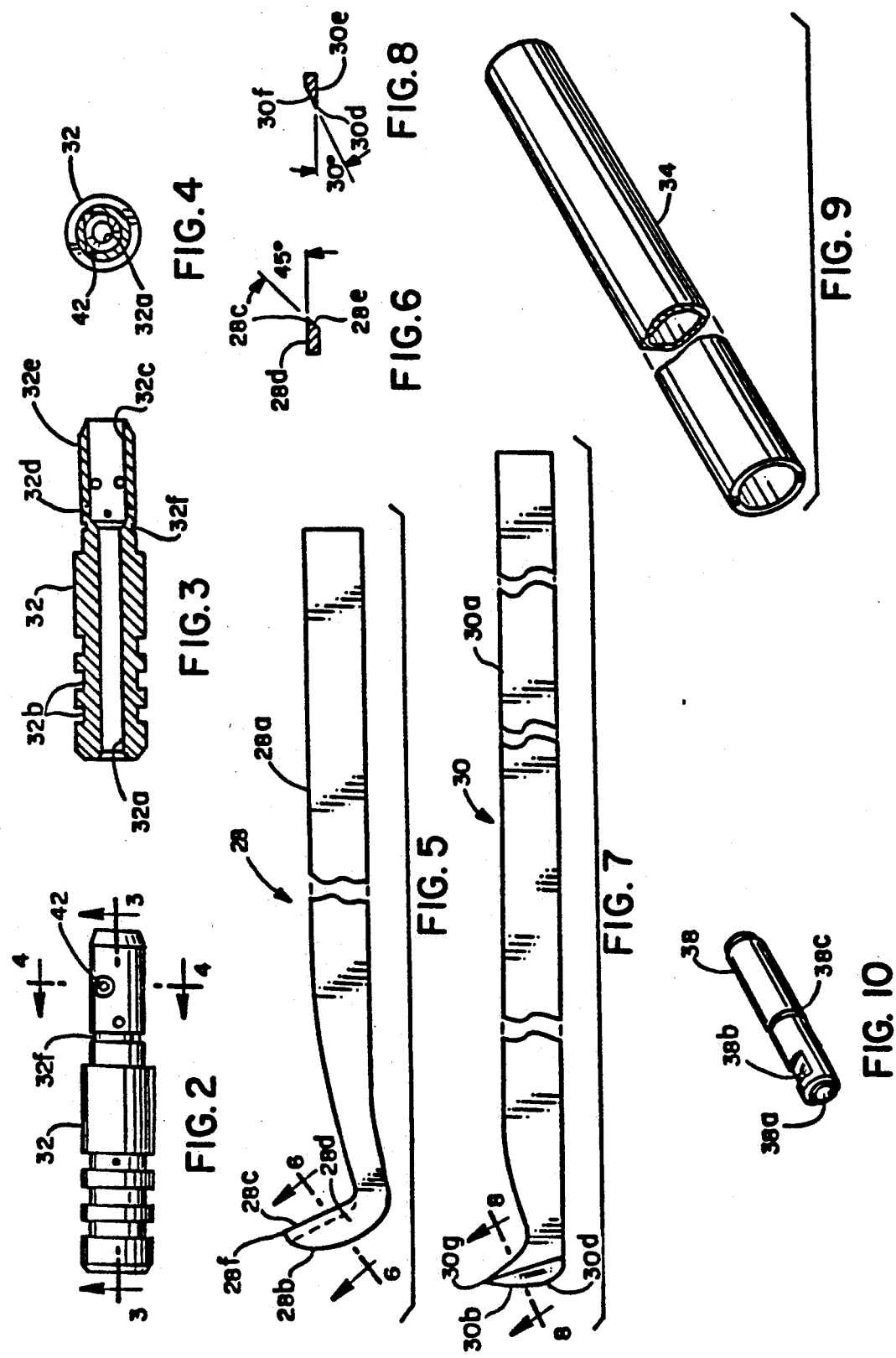

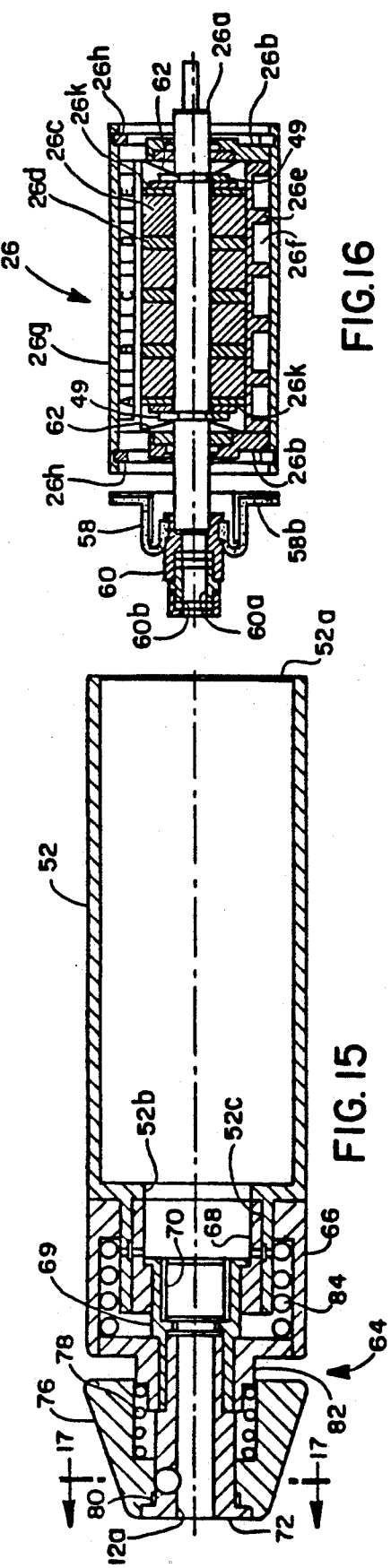
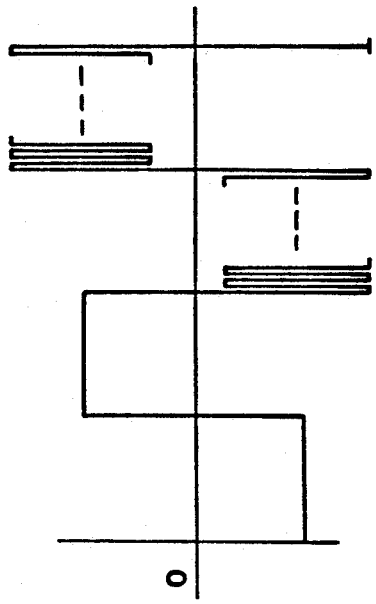
FIG.16
FIG.14
FIG.15
FIG.17
FIG.18

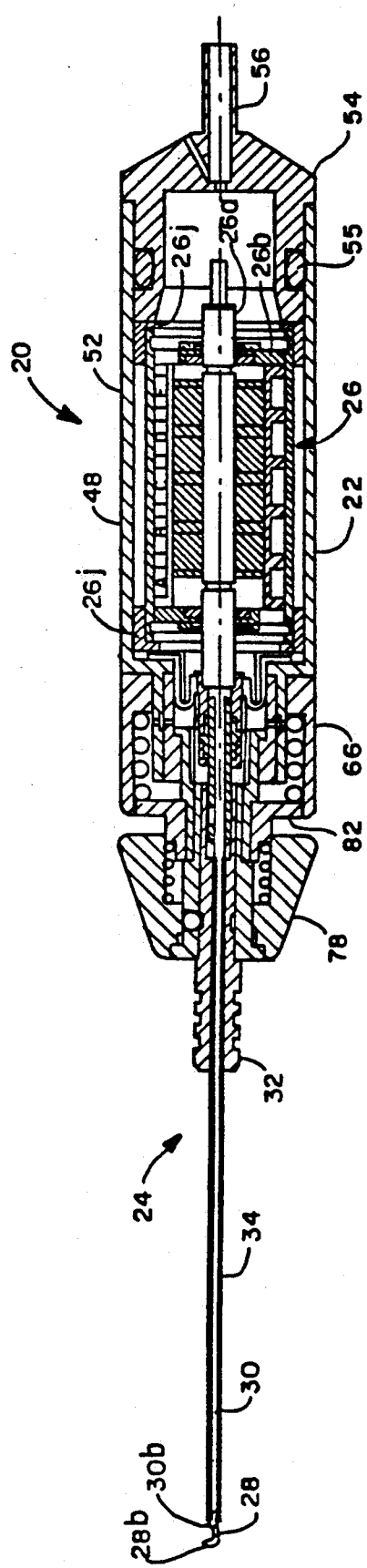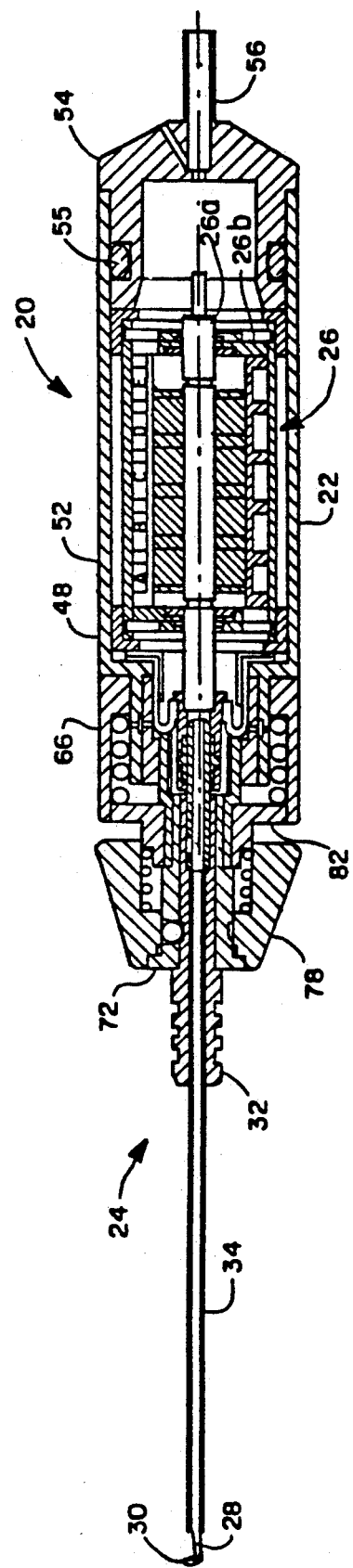
FIG. 19
FIG. 20

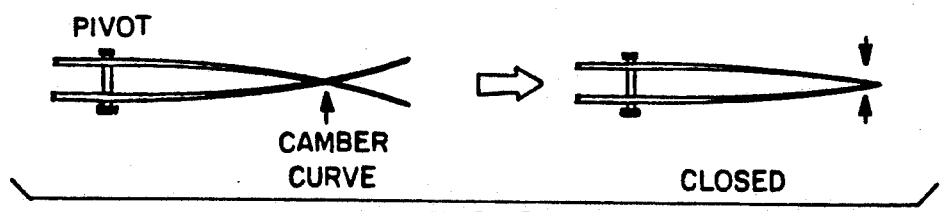
FIG. 29
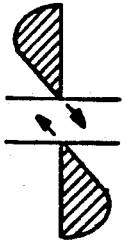
PREFERENTIAL WEDGE PATH
FIG. 30
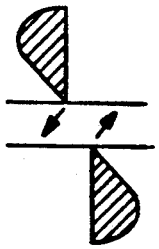
GUIDANCE CAMBER PATH
FIG. 31
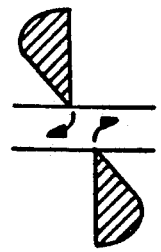
ACTUAL TWISTING MOTION TO BLADES
FIG. 32
RESULTING CUT
SOFT OR THICK TISSUE
HARD OR THIN TISSUE
FIG. 33
BLADES BEGIN CUT 0.030 INCH APART
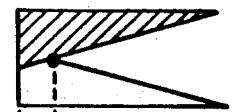
BLADE MOVES UP 3MI SO THAT BLADES ARE 0.027 INCH APART
THE CUTTING POINT MOVES FORWARD ONLY .003 INCHES.
FIG. 34
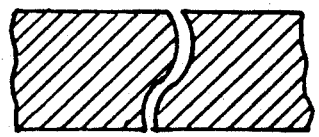
"S" SHAPE CUT TO CONVENTIAL PRIOR ART OCCLAR SCISSORS
FIG. 35a
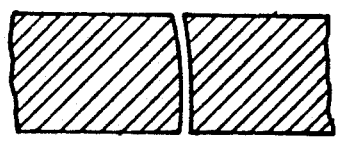
PERPENDICULAR CUT TO PRESENT INVENTION SCISSORS
FIG. 35b

INTRAOCULAR SURGICAL SCISSORS

BACKGROUND OF THE INVENTION

This invention relates to an improved intraocular surgical instrument which can be used with microsurgical scissors, forceps, knives and the like.

The invention will be described in connection with its preferred usage and that is a microsurgical scissor. Microsurgical scissors are in widespread use during intraocular operations by surgeons worldwide. Three types of driver (actuation) systems for these scissors are in current use: manually operated handles with squeeze-type or lever depression actuation, pneumatic piston linear drivers, and electrical motors of direct current or solenoid drive.

Grieshaber and Co., A.G. of Switzerland produces a wide variety of microsurgical scissors and driver systems including the Proportional Control System (PCS), a Membrane Peeler Cutter (MPC) and manual drive handles (Southerland Style). Pneumatic drivers are produced by Storz Instrument Co. of St. Louis, Mo.; Alcon Surgical, Inc. of Ft. Worth, Tex.; The Dutch Ophthalmic Research Corporation (DORC) of Holland; and TREK Medical of Muckwamago, Wis. Each company provides various scissortips attachable to these drivers, or allow them to cross adapt to other manufacturer's designs. Manual handles are provided by Grieshaber, Alcon, Storz, DORC, TREK and others.

Most intraocular scissors have design similarities in which a pair of cutting blades extend from the end of a tubular needle with one blade being fixed and the opposite opposing blade end being reciprocated between an open and closed position with respect to the fixed blade. This reciprocating movement is accomplished through the action of one of the three above-listed driving systems, i.e. manual, pneumatic or motor.

In the manual driver, actuation of one blade end against the other is through the transfer of movement to the movable blade by depression of a single lever extending from the handle (Southerland-Grieshaber) or by squeezing two opposing platforms on opposing sides of the handle. The movable blade moves through an excursion of 60 to 70 mils (0.060 to 0.070 inch) from the fully open to the fully closed portion during actuation.

In the pneumatic driver, actuation is achieved by pressurizing a piston with a compressed gas source into a chamber within the handle, which causes the piston to move forward against a spring, moving the one blade against the other, closing the blades. Opening the blades is accomplished by movement in the opposite direction through energy stored in the spring, as the gas within the piston chamber is released. Control of the gas pressure release to the piston is accomplished by depression of a foot pedal by the surgeon. Scissor actuation is thus accomplished via footpedal control rather than via finger control, allowing the surgeon to hold the instrument steady without inducing any unnecessary tremor or motion to the blades due to finger movement. The footswitch is a linear depression switch which also allows selection between a "proportional cut" mode versus a "multicut" mode by the manufacturer. In the "proportional cut" mode, the scissors blades close at a rate and position directly related to the rate and position of depression of the pedal, e.g. one-half depression of the pedal will close the scissors half way, full depression will close the scissors fully, etc. The scissors will move open and closed inducing a cutting force only as the footpedal is depressed and released, with a more rapid depression resulting in a more rapid closure, etc. A full depression of the footpedal by the surgeon closes the blades to reduce the width of the scissor blade profile so that it can be inserted through a small slit, e.g. 1.0 mm slit, in the eyeball. Once within the eyeball, the scissor blade can be opened and closed by the footpedal action described above. To remove the scissors from the eyeball, the blades are fully closed by complete depression of the footpedal to again reduce the scissor width. In the event of failure of the piston driver while it is in the eyeball, the surgeon can manually close the scissors in this emergency situation by screwing a thumbscrew down on the driver to allow its safe removal from the eye. While the scissors are in the eye, the surgeon can select the "multi-cut" mode by the temporary lateral motion of the footpedal. Depression of the pedal in this mode causes movement of the blade from its open to its closed position and back to its open position repetitively at a rate of approximately one stroke per second. A slight depression of the footpedal activates this multiple repetition mode, which continues at the same rate regardless of the amount of depression to the pedal. The surgeon returns to the "proportional cut" mode and fully depresses the pedal to fully close the scissor blades and holds them closed to remove them from the eye.

Motor drivers of either rotary or linear solenoid style activate scissor closure by controlled transfer of the motor energy to the movable blade. The MPC is an automated solenoid-style microscissors that has a non-detachable pair of cutting blades extending from the end of a tubular needle, with the outer blade end being fixed and the inner blade end being reciprocated between an open and closed position with respect to the fixed blade. A first footswitch is operated by the surgeon to move the movable blade to a closed position reducing its profile allowing its introduction into the eye. Once inside the eye, the first footpedal is released and the movable blade snaps open due to energy stored in a spring within the driver handle. Depression of a second footpedal causes the blades to move from an open position to a closed position against a spring, and then back to an open position. The scissors always default to an open position during activation of the second footpedal. The blade excursion is again 60 to 70 mils (0.060 to 0.070 inch) and travels at a rate of 1000 mm/sec from the open to the closed position. The moving blade cuts in about 5 milliseconds and remains shut for about 15 milliseconds before automatically returning to the open position. The MPC can also be operated in a "single cut" mode versus a "multicut" mode. In a single cut mode, depression of the second footpedal results in one excursion of the movable blade and one resulting cut. Release and redepression of the second footpedal is required to initiate a second excursion and cut. In the "multicut" mode, hereinafter referred to as an oscillation or oscillatory mode, the blade moves through a series of repetitive cuts or oscillations at a rate of one to five strokes per second, with each stroke traveling at 1000 mm/sec. These oscillations continue While the second footswitch is held in the depressed position. This MPC microsurgical scissor is gas sterilizable and is not recommended to be steam autoclaved, except in "emergency situations", as would be desirable for an intraocular scissor.

In the PCS-Grieshaber system, there is a power operation and control of a variety of Southerland intraocular instrument tips including a scissor by energy from a DC motor within the handle. This PCS system includes movement of the cutting blade in either the "single" stroke cutting mode or a continuous oscillatory motion mode. Manual selector switches allow choice between these modes, as well as selection of the rate of scissor closure for either mode, and the rate of oscillations in the oscillatory mode. Additionally, a manual dial switch allows the opening distance between the radius of curvature of the blades to range from ⅓, ⅔ or full.

In the MPC automated microscissors and in some other Southerland and manual scissors, the scissor tip is of the vertical design in which the outer fixed blade has a cutting edge substantially parallel to the cutting edge of an inner movable blade such that the cutting edges cut on a substantially straight line on a guillotine principle. The surfaces are not perfectly parallel, however, and do have some angle between them, creating a cutting point where the blades are in contact. The MPC scissors close so quickly, however, that their cutting point is effectively a straight line rather than a single point as in conventional angled scissors described below.

Shear is a force responsible for division of the tissue held within the scissor blades regardless of their design, and describes a vector perpendicular to the vector of movement of the direction of closure to the blades. The strength of the force vector pushing the blades one against the other is responsible for the creation of the shear force vector.

Guillotine or parallel blade scissors tend to crush the tissue between the blades before the shear begins to divide the tissue. This crush action has an advantage of holding the tissue within the blades and preventing forward thrust of the tissue out from the blades. It has a distinct disadvantage, however, of creating crush artifact in the tissues due to tissue deformation that occurs prior to its shearing, as illustrated in FIGS. 25 and 26 hereinafter. Due to motion of the scissors between cuts and the inability to begin a cut immediately in the exact same position as the ending of the previous cut, the tissue is engaged in a slightly different location, resulting in steps or shoulders between cuts and also in curved or scalloped surfaces on the cut tissue wall, as shown in FIGS. 25 and 26. Parallel or vertical-style scissors manually driven exhibit the same tissue sectioning artifacts as the MPC microsurgical scissor and is shown in FIG. 22.

Angled or horizontal-style scissors can be manually or automatically driven depending on the manufacturer, but the cutting characteristics are similar, and different from vertical scissors. In angled scissors, the blades pivot from a fulcrum point and create a single cutting point where the blades are in contact. When the blades are fully open, this point is closest to the fulcrum and successively moves forward down the scissor blades toward the tip as the scissor closes. The blades also become relatively more parallel as they close and begin to induce some crush action near the tip.

As the forward movement of the cutting point proceeds toward the tips of the blades it induces a forward thrusting motion to the tissue due to the resistance of the tissue being sheared, thus serving to push the tissue ahead of the scissor as it closes. Also, a greater area of tissue is included between the blades during closure, further increasing tissue resistance and thus contributing to increased forward thrust. Forward thrust of tissue during ocular surgery is annoying and clinically undesirable as it contributes to irregular cuts and longer procedures. Needing to "chase" the target tissue puts additional traction on surrounding normal tissue and contributes to tears and accidental cuts within the normal tissue.

With a force applied about the fulcrum of the scissors blades the shear forces are at a maximum when the cutting point is nearest to the or fulcrum point of the blades. The blades will stay together with the greatest force near the pivot and thus shear is maximum here. Further, less force is required to close the blades to create this shear force when the cutting point is near the pivot. As the cut proceeds and the cutting point moves farther from the pivot, mechanical advantage is lost, greater forces are required to close the blades, shear force is lost and the scissor blades may actually be pushed apart at the tips if the tissue resistance force becomes greater than the shear force.

In order to maintain a force pushing the blades together at the cutting points, the blades are positioned against each other by two opposing forces called camber. The radius of curvature of the camber increases along the length of the blade, to create more shear force at the tip to try to overcome some of the loss of shear force due to the loss of mechanical advantage, as shown in FIG. 29.

In cross section, scissor blades are actually asymmetric wedges opposed to each other, and each want to drive into the tissue at an oblique angle called the "preferential wedge path" (FIG. 30). The camber and closing movement of the blades want to drive the blades into the tissue 60° to 90° away from the wedge path (FIG. 31). The resulting actual movement of the blade is more of a twisting motion as shown in FIG. 32. Because the tissue has resistance to shear, it too will be twisted, more or less by the twisting motion of the blades with softer and thicker tissues twisting and deforming more than harder and thinner tissues. The resulting cross sectional cut has an "S" shape rather than being perpendicular to tissue surface, as shown in FIG. 33. Ocular tissues are usually soft enough to result in "S" shape cuts by conventional scissors, which is less desirable due to its irregular surface, as shown in FIGS. 23 and 24.

As more of the blade surface becomes buried within the tissue during the cut, the lateral resistance increases, preventing a side-to-side motion or a "steering" redirection to the scissors. If the scissors are wide open, the lateral resistance is at a minimum and the scisors can be steered to a new location without distortion induced by lateral resistance.

Every microsurgical scissor currently available for ocular surgery has more or less of the following disadvantages dependent on its individual design: (1) forward thrust during closure pushes the target tissue out of the scissor because of forward motion of the cutting point; (2) crush artifact deforms the tissue during shear; (3) irregular "S" shaped cross-sectional cuts occur, the severity of which is determined by individual ocular tissue characteristics; (4) loss of mechanical advantage during closure causes loss of shear, creating tissue incarceration at the tips, and resultant lateral crush artifact; and (5) increased lateral resistance during closure prevents re-direction of the scissor along a curved line without creating crush and distortion artifact into the cut.

STATEMENT OF THE INVENTION

The present invention provides a scissor tip design and actuation which alleviates all of the above disadvantages thereby resulting in a much more controlled, efficient and uniform shearing action to the tissue.

The present invention has vertical scissor blades in the sense that the movable blade reciprocates in the needle shaft and the movable blade edge projects at substantially a right angle to the blade portion connecting to the driver. Rather than having a guillotine, parallel line cut simultaneously across the entire blades as in the MPC scissors, the blades are curved to diverge from each other so that a wide open space is defined between the free ends of the scissor blades prior to its complete closure, which further serves to funnel tissue to the cutting point.

The present invention is directed to providing an improved cut from an intraocular instrument such as a scissors and, as illustrated in FIGS. 27 and 28, hereinafter, provides a cut with no significant steps or shoulders between successive cuts as shown in the illustrations made with the prior art scissors. Also, there is no need to physically hold the tissue to overcome forward thrust. For reasons to be explained, one would like to cut at a frequency higher than the natural resonant frequency of the tissue. Operating above tissue-resonant frequencies utilizes tissue inertia in which it will shear or cut before it will resonate or move forward. The material frequency of tissue is defined by the formula:

$$f = \sqrt{\frac{K(\text{stiffness})}{\text{mass}}}$$

From the formula, it is seen that the stiffer the tissue and the lower the mass, the higher will be the tissue resonance (f). Ocular tissues have very low mass and variable but usually moderate stiffness and thus a relatively high resonant frequency.

The present invention provides a vibrating mode of operation in which the movable scissor blade are moved one against the other at a high frequency, e.g. 200–800 cycles per second, and through a low excursion, e.g., 1–10 mils, to allow operation in excess of the natural resonance of living tissue. This rapid vibration serves to create tremendous shear forces where the blades contact.

When the vibration actuation to the blade closure is accompanied by a forward, manual push of the scissor into the tissue, the greatly increased shear forces cut the tissue as the surgeon glides the scissor through it. The funneling action of the partially opened scissor tips cause the tissue to be evenly directed to the rapidly vibrating cutting point, causing the tissue to be cut without "steps".

The vibratory cut is made with the scissor blades partially open, e.g. if the entire movable blade excursion is about 0.060 inch between the open and closed positions, the blades may be open only 0.030 inch and a vibratory excursion of the movable blade will reduce the opening to 0.027 inch opening and then returning the opening to 0.030 inch dimension.

Since the excursion of the blades is minimal, e.g. the range of 3 mil, the forward movement of the cutting point is also quite minimal, the amount of which is determined by the angle and geometry of the scissor blades. On average the cutting point moves forward and backward with each rapid excursion only 1 to 5 mil, as shown in FIG. 34. Since the forward movement of the cutting point is clinically negligible, forward thrust of tissue is negligible. Since the scissor are operating with the tips more open, the amount of tissue within the cutting surfaces is minimal, further decreasing tissue resistance and further reducing forward thrust. This shear action without forward thrust in non-parallel scissors is not heretofore available in intraocular scissors.

Since shear is created continuously with the vibration action near the pivot point of the blades, the mechanical advantage of the system is at a physical maximum. With increased mechanical advantage, less force is required to sect the tissue during the cut. This maximization of mechanical advantage does not exist in prior art intraocular scissors. Preferably, the scissors handle body is round and tubular and is held between the forefinger and thumb so that the direction of cut may be easily made by the surgeon spinning the tubular handle body to re-direct the cutting edges.

Since the present invention scissor is capable of creating continuous shear with the scissor blades relatively wide open, the cutting point acts as a true functional static point rather than a moving or kinetic point. Less scissor blade is buried within the tissue and lateral resistance is minimized, allowing the scissor to be steered and continuously re-directed within the tissue if necessary. This ability to redirect scissors without lateral distortion artifact does not exist in prior art intraocular scissors.

The excursion of 3 mils occurring 500 times per second creates adequate and uniform shear, allowing the surgeon to push the "relatively non-moving" cutting point against the tissue, separating and cutting the tissue without the large steps, without large crush artifact and without large "S" shape cross-section cuts in the wall, as in FIGS. 25 and 26, as was noted in the prior art intraocular scissors seen in FIGS. 20 through 24. The lack of the "S" cross section despite the softness of the tissue is due to the fact that the preferential wedge path and the movement guidance paths are relatively uniform due to the extremely small excursion, and minimal twist to the blades.

Importantly, the frequency of vibration of the blades is higher than the natural tissue resonance, and thus inertial forces keep the tissue from twisting as the shear continues through its thickness, as diagrammed in FIGS. 35a and 35b and as was noted clinically, comparing FIG. 21 to 26.

The present invention also provides a cutting mode having both the oscillatory and the vibratory cutting action. As explained above, if the movable blade oscillates between its open and closed position several times a second, e.g., four to five times to complete a full excursion of 0.060 inch, the blade may also be vibrated to move through the small vibratory excursions of 0.001 to 0.003 at a frequency of 200–800 cycles per second. This is a combined or multi-operation of both oscillatory and vibrational movement simultaneously of the cutting edges; this cutting action was not heretofore available in intraocular scissors.

These surgical intraocular instruments are small and lightweight and must operate in a surgical environment and preferably should be steam autoclavable. To obtain the frequency desired, it was found necessary to develop an electromagnet drive operating at a frequency exceeding substantially the usual 60 Hz. In addition to being able to provide a low frequency drive for the oscillatory mode in the range of 1-5 cps, it was also desired that vibration drive at this high frequency, preferably at about 500 Hz, and a low excursion of about 1 to 10 mil. be superimposed on the larger excursion of e.g., 0.060 inch at the low frequency to vibrate the solenoid at a high frequency. This has been accomplished by the use of a DC signal to drive the solenoid in the oscillatory low frequency mode and to superimpose thereon an A.C. signal of high frequency. The AC signal was formed into a square wave to achieve the vibration reciprocatory movement desired. A small mass is needed for the solenoid and the movable cutting blade in order to achieve the acceleration, deceleration and reversal of movement. Also, it is desirable that the deceleration of the cutting blade and solenoid be made smooth, as with a shock absorbing action, and that the reversal of direction and acceleration in the opposition takes place without a jerky operation that would be felt by the surgeon. A further consideration is to have the movable blade at its open position at the end of a cutting operation so that the surgeon's next movement of the scissors is not accompanied by the tissue tearing where it is caught between closed scissor blades. Another consideration, for a commercially desirable intraocular instrument such as a scissors using a reciprocating solenoid, is that the reciprocation does not induce a positive pressure that would blow air into the eye; and, on the other hand, does not produce a vacuum that would suck tissue into the hollow needle in the space between the blade and the surrounding annular wall of the needle.

The driver of the intraocular instrument may be provided with a hollow shaft through the solenoid and provided with an attached infusion tube to inject liquid into the eye. The preferred driver has a connection or coupling that it allows it to be used with a number of surgical tools, e.g., disposable intraocular scissors, an intraocular forceps, intraocular trephine, or reciprocating knife or shear. Also, the preferred driver has its solenoid structure sealed to moisture so that it can be steam autoclaved and reused with any of these other intraocular instruments.

Accordingly, a general object of the invention is to provide a new and improved intraocular, microsurgical instrument of the foregoing kind usable with one or more intraocular tools.

A further object of the invention is to provide a vibratory intraocular scissors.

A still further object of the invention is to provide an intraocular scissors that oscillates between open and closed positions at a low frequency and that also has a small vibratory motion at a substantially higher frequency.

BRIEF DESCRIPTION OF THE DRAWINGS

FIG. 1 is an exploded sectional view of an intraocular surgical scissors embodying the invention;

FIG. 2 is a side elevational view of a bushing which provides the support for the scissors blades as shown in FIG. 1;

FIG. 3 is a sectional view taken along line 3—3 of FIG. 2;

FIG. 4 is a sectional view taken on line 4—4 of FIG. 2;

FIG. 5 is an enlarged fragmentary side elevational view of the stationary cutting blade used in the scissors of FIG. 1;

FIG. 6 is a sectional view taken on line 6—6 of FIG. 5;

FIG. 7 is an enlarged fragmentary side elevational view of a portion of the movable blade member of the scissors of FIG. 1;

FIG. 8 is a sectional view taken on line 8—8 of FIG. 7;

FIG. 9 is an enlarged perspective view of a portion of the tube or needle which supports the blade members in the scissors of FIG. 1;

FIG. 10 is a perspective view of the sleeve which supports and drives the movable blade member of the scissors of FIG. 1;

FIG. 14 is a diagram of the voltage wave form applied to the motor under various modes of operation;

FIG. 15 is a sectional view of a portion of the handpiece of the scissors of FIG. 1 with the motor removed;

FIG. 16 is a sectional view of the motor of the scissors of FIG. 1;

FIG. 17 is a sectional view taken on line 17—17 of FIG. 15;

FIG. 18 is a sectional view taken on line 18—18 of FIG. 17;

FIG. 19 is a cross-sectional view of the surgical scissors of FIG. 1 showing the cutting blades in the full open position;

FIG. 20 is a cross-sectional view identical to FIG. 19 but showing the cutting blades in the closed position;

FIG. 29 is a schematic diagram of the scissors blades in various positions;

FIGS. 30, 31 and 32 are diagrams of the forces acting on scissors blades;

FIG. 33 is a sketch of scissors cut on various types of tissue;

FIG. 34 is a pair of diagrams illustrating the change in cutting point position under a vibrating mode; and FIGS. 35a and 35b are sketches of a prior art tissue cut and a cut by the scissors of the present invention.

DETAILED DESCRIPTION OF THE PREFERRED EMBODIMENT

Figure 11A:
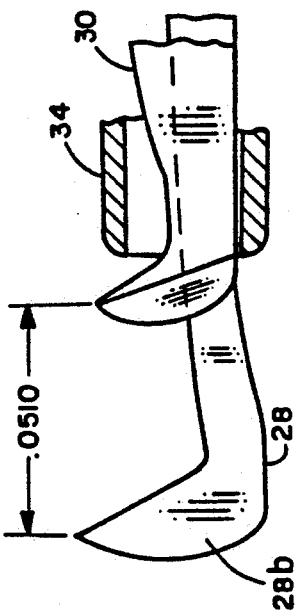
FIGS. 11a, 11b and 11c are schematic showings of the blade portions of the scissors of FIG. 1 showing the blades in their closed, partially opened and fully opened positions, respectively.

Referring to FIGS. 1, 19 and 20 of the drawings, there is shown an intraocular surgical scissors embodying the invention and designated generally by reference numeral 20. The scissors 20 includes a handpiece 22 and a detachable assembly 24 with a motor means 26 provided to power the scissors 20.

Considering first the detachable assembly 24, it includes a stationary blade member 28, and a movable blade member 30. To support the blade members 28 and 30, there is provided a bushing 32 which is generally cylindrical in shape, having a central bore 32a within which a tube 34 is supported. The tube 34 serves to support and enclose the blade members 28 and 30 and is formed of 20 gauge stainless steel needle. The tube or needle 34 is fixedly secured to the bushing 32 by a pin 36, which is press fitted in aligned openings in the tube 34 and in the stationary blade member 28. As shown in the upper portion of FIG. 1, the bushing 32, the tube 34 and the stationary blade member 28 are fixedly secured together by the pin 36. To facilitate removal of the assembly 24 from the handpiece 22, the outer surface of the bushing 32 is formed with annular grooves 32b which facilitate grasping the assembly 24 to withdraw it from engagement with the handpiece 22.

As shown in FIGS. 1 and 5, the stationary blade member 28 includes an elongated portion 28a which is received within the tube 34 and also includes a laterally extending blade 28b. The blade 28b is provided with a cutting edge 28c which extends along the edge of the blade 28b which is facing toward the elongated portion 28a. The cutting edge 28c is formed by the intersection of flat sidewall 28d of the stationary blade member 28 and a beveled surface 28e, the planes intersecting at an angle of about 45°. As shown in FIG. 5 and in the schematic views of FIGS. 11a, 11b and 11c, the cutting edge 28c is slightly concave in configuration and extends at an angle of about 60° to the lengthwise axis of the tube 34. It is also noted that the stationary blade member 28 terminates at a pointed end 28f, and the outer surface of the blade 28b is formed with a gently curved surface which connects to the lengthwise extending back edge of the blade 28b.

The movable blade member 30, which is also a part of the detachable assembly 24, is supported for reciprocation within the tube 34 by a sleeve 38 which is secured to the blade member 30 by means of a pin 40, press fitted into aligned openings in the sleeve 38 and the blade member 30. The sleeve 38 includes a bore 38a within which the end of the blade member 30 is received. In addition, the sleeve 38 is formed with a cutout area 38b which provides clearance for the sleeve 38 to reciprocate with respect to the bushing 32 and a limit pin 41 which is press fitted into aligned openings 42 in the bushing 32, as shown in FIGS. 2 and 4. The pin 41 in the bushing 32 engages the opposite ends of the cutout 38d, thus limiting the distance through which the sleeve 38 may reciprocate with respect to the bushing 32.

The movable blade member 30 includes an elongated portion 30a and a transversely or laterally extending blade 30b. There is formed on the elongated portion 30a a slot 30c through which the pin 36 extends. The slot 30c provides clearance to permit the movable blade member 30 to reciprocate with respect to the stationary blade member 28 and the bushing 32. Thus, the movable blade member 30 and the stationary blade member 28 must be assembled together into the bushing 32 and tube 34 before the assembly pin 36 is inserted to mount the tube 34 and the stationary blade 28 with respect to the bushing 32. Thereafter, the sleeve 38 may be inserted into a bore portion 32c to permit insertion of the assembly pin 40 to secure the movable blade member 30 with respect to the sleeve 38. As shown in FIG. 3 there are clearance openings 32d in the bushing 32 to permit insertion of the assembly pin 40 into the aligned openings in the sleeve 38 and movable blade member 30.

Figure 11B:
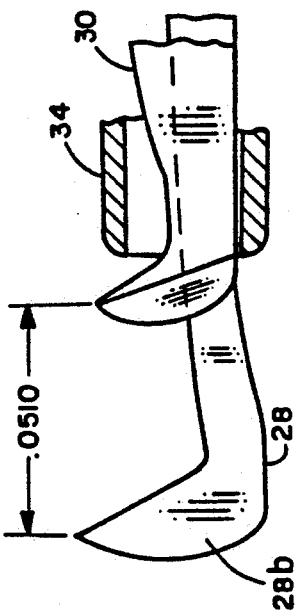
Figure 11C:
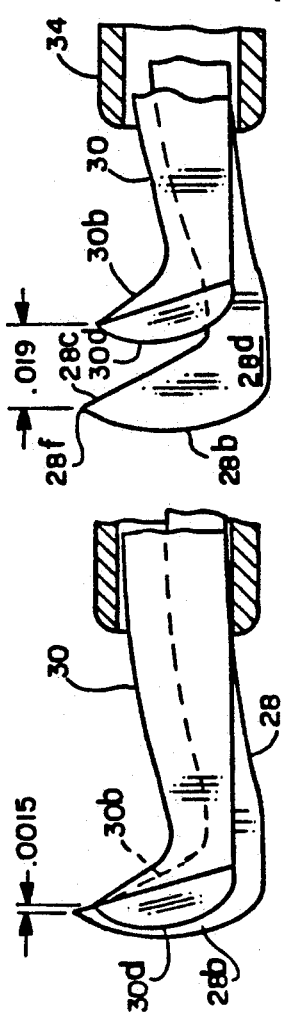

The end of the movable blade member 30 remote from the end to which the sleeve 38 is attached includes the blade 30b, which is best shown in FIG. 7 and the schematic views of FIGS. 11a, 11b and 11c. The blade 30b has a cutting edge 30d formed on the outer edge of the blade 30b rather than on the inner edge as is the case with the cutting edge on the stationary blade 28b. The cutting edge 30d has a convex curvature, while the cutting edge is at substantially right angles to the axis of the elongated portion of the blade members. As shown in FIG. 8, the cutting edge 30d is defined by the side surface 30e and the beveled surface 30f of the blade 30b. The surfaces 30e and 30f define an angle of about 30° which terminates at the cutting edge 30d. The cutting edge 30d terminates at the outer end of the blade 30b at a pointed tip 30g. The blades 28b and 30b are shown in their fully closed position in FIG. 11a. In FIG. 11b, the blades are shown in their open position at which the shearing engagement between the cutting edges 28c and 30d commence. In FIG. 11c, the blades are shown in their fully open position in which the cutting edges are widely spaced from each other. In the closed position with the cutting edges completely covered by the adjacent blade, the assembly may be moved into position with a minimum of damage or cutting of adjacent tissues. In the starting-to-cut position of FIG. 11b, there is a very small angle at which the cutting edges 28c and 30d intersect or extend across each other, thereby reducing the tendency of the scissors to displace tissue which is to be cut. The curvature of the movable blade 30b has a tendency to hold the tissues while cutting rather than displacing them from between the two blades. The configuration of the cutting edges 28c and 30d is very important in the various modes in which the scissors 20 may be operated, as will be explained in greater detail below. The diverging nature of the cutting edges as positioned in FIG. 11b is useful in gathering in tissues to be cut as the blades move forward. At the same time, the very acute angle at the point where the cutting edges 28c and 30d intersect or cross is important in providing a cutting action in which there is little outward thrust against the tissue being cut as the blades move together.

The handpiece 22, as shown in FIGS. 1, 19 and 20, is adapted to receive, support and drive the detachable assembly 24. The handpiece 22 comprises a housing 48 which provides an enclosure for the motor 26. The motor 26 is a linear velocity-to-displacement transducer and is also known as a linear solenoid, linear motor or linear actuator. It is of low mass and low reluctance so that it may perform the functions of driving the blade 30 in its various modes of operation to be described below. Through the use of rare earth magnets of low mass, the motor may be operated to oscillate and vibrate the scissors 20 at frequencies from 1 to 1000 Hz. The low mass of the armature of the motor 26 is necessary to permit movement at these velocities.

The linear motor 26 includes an axially displaceable shaft 26a which is mounted for sliding movement in bearings in end plates 26b. Affixed to the shaft 26a are a plurality of magnets 26c which are separated by spacers 26d. The magnets are preferably made of HI-MU 80 material which is a rare earth alloy magnet material available commercially. This material may be magnetized to provide a strong magnetic field for a given weight and has the capacity to retain its magnetization over time and when heated to high temperatures for short periods, as during steam autoclaving for sterilization. The magnets are polarized with axially spaced poles arranged with their respective magnetic fluxes combining. The magnets 26c are secured against axial movement on the shaft 26a by resilient C-rings 49 received in annular grooves in the shaft 26a. Surrounding the movable armature, including the shaft 26a and the magnets 26c, is a coil bobbin 26e which supports five spaced coils 26f. The coils are arranged and connected in circuit in a known manner so that the armature is displaced with a force proportional to the signal applied to the field coils. The coils 26f and the end plates 26b are supported by a casing or shell which is also formed of the MU-80 to provide a low reluctance magnetic circuit 26g. The end plates 26b and the coil bobbin 26e are retained within the casing 26g by E-rings 26h which are received within annular grooves in the ends of casing 26g, to restrain the parts from axial displacement.

In order to support the motor 26 within the housing 48, there are provided annular shouldered rings 26j as are best shown in FIG. 1. The housing 48 is formed by a cylindrical member 52. As best shown in FIG. 15, cylindrical member 52 has an open end 52a through which the motor 26 is assembled, and which open end is closed by a cap 54 which has an opening through which a power cord 56 extends for connection with the coils 26f of the motor 26. An O-ring seal 55 is positioned between the cap 54 and the cylindrical member 52 to seal the motor enclosure against the entrance of moisture. The cord entrance through the cap 54 may be sealed with silicone, RTV or epoxy in a conventional manner.

The forward end of the cylindrical member 52 is formed with an annular wall that defines an opening 52b through which one end of the motor shaft 26a extends forwardly. In order to seal the motor shaft with respect to the housing opening 52b, there is provided a flexible boot 58 which has an outer flange 58b, which is clamped between the cylindrical member 52 and the annular support ring 26j. The sealing boot 58 is in sealed engagement with a coupling member 60 at its inner diameter, as shown in FIG. 16. The boot 58 permits the shaft 26a to reciprocate axially while sealing the opening 52b against the entrance of moisture into the motor enclosure. The coupling member 60 is formed with an inner bore 60a which is adapted to receive and drivingly connect the sleeve 38 to the armature shaft 26a. Within the coupling 60 there are O-ring seals and a resilient C-ring 60b which is adapted to snap into engagement with a corresponding annular recess 38c formed in the sleeve 38. Thus, when the assembly 24 is inserted axially into the handpiece 22, the sleeve 38 enters the coupling 60 as shown in FIG. 6, and the C-ring 60b snaps into engagement with the annular groove 38c in the sleeve 38 to provide a detent action in retaining the movable blade member 30 coupled to the armature shaft 26a. As the motor is actuated by an alternating current to provide high frequency vibration, the armature shaft 26a reciprocates axially, thereby driving the movable blade member 30 through the sleeve 38. During this motion of the armature a pair of springs or Belleville washers 62 mounted on the armature shaft 26a are alternatively compressed against the end plates 26b as the armature shaft 26a moves forward and backwardly in its mounting bearings. The springs 62 tend to reduce the shock or bouncing that would otherwise occur at the extremity of travel of the armature and also provide a centered rest position of the armature when the motor is not energized.

In order to mount the assembly 24 on the handpiece 22, there is provided a latch mechanism 64 which is supported on a cylindrical wall 52c which extends from cylindrical member 52. An outer spring enclosure 66 and an inner support 68 are each secured to the outer diameter and inner diameter respectively of the cylindrical member or wall 52c. The inner support 68 receives for axial sliding movement a bearing support 69 to which is secured a bearing 70 for slidably supporting the coupling member 60, as is evident from FIG. 1. Affixed to the bearing support 69 is a tubular member 72 which has an internal bore 72a adapted to slidably receive the bushing 32 to mount the assembly 24 with respect to the handpiece 22. The bushing 32 is formed with a reduced diameter portion 32e which is received within the bore 72a.

In order to retain the bushing 32 within the bore 72a, there are provided a group of three detent balls 74, which are received within openings 72b formed in the tubular member 72. The openings 72b are tapered so that the balls 74 may project into bore 72a but may not move inwardly beyond the position shown in FIGS. 17 and 18. A camming member 76 is mounted on the exterior of the tubular member 72, to retain the detent balls 74 within the tapered openings 72b. The camming ring 76 is biased to a forwardmost position by a helical spring 78. With the application of pressure on the camming ring 76, it may be displaced axially, compressing the spring 78 to move the ring 76 to a point where relief openings 80, as best shown in FIG. 18, permit the balls 74 to move outwardly, thereby releasing the engagement with a annular groove 32f formed in the bushing 32. In order to assemble or disassemble the assembly 24 from the handpiece 22, it is necessary to move the camming ring 76 inwardly or to the right as shown in FIG. 1 to thereby permit the balls 74 to move outwardly and accept the end of the bushing 32.

The tubular member 72 is attached at its inner end to the bearing support 69 which is secured to a flanged member 82 having its peripheral inner end in engagement with a coil spring 84 received within the cylindrical spring enclosure 66 for a purpose to be explained more completely below. The bearing support 69 secured to the tubular member 72 is supported for axial sliding movement by inner support 68 and thereby permits the tubular member 72 to be displaced axially. As a consequence of the sliding bearing engagement between the support 69 and the member 68, when an inward force is applied to the tubular member 72, through the bushing 32, the assembly, including the tubular member 72, the flanged member 82 and the support 69 may be moved axially inwardly or to the right as viewed in FIG. 1. This movement in effect causes the stationary blade member 28 to be moved with respect to the movable blade member 30, which, of course, is attached to the armature shaft 26a.

It is important for safety reasons to provide means for causing the blades 28b and 30b to be positioned in overlapping relationship in the event of a power failure to the handpiece 22. If, during a surgical procedure the power were to be interrupted, the springs 62 would locate the movable blade member 30 in a center position with the cutting blades 28b and 30b spaced apart as in FIG. 11b, making it difficult for the surgeon to remove the scissors 20 from the eye of a patient. Accordingly, it is necessary that means be provided to move the blades to the overlapping position as shown in FIG. 11a. The latch mechanism 64 permits the operator to grasp the bushing 32 or the forward portion of the tubular member 72 to press the assembly 24 inwardly, thereby moving the stationary blade 28b in line with the movable blade 30b, which would otherwise be in a central position.

As discussed above, it is contemplated that the handpiece 22 may be used with a variety of other surgical tools that require a solenoid or oscillatory drive of this type. Such instruments would include in addition to intraocular scissors, vitrectomy instruments, intraocular forceps, intraocular trephine, reciprocating or vibrating knife or shear. It may be desirable and is contemplated that liquids might be injected into, or tissue withdrawn from, the eye through a passageway extending axially of the shaft 26a.

In order to prevent the unwanted withdrawal of liquid or tissue through the tube 34 or the possible pumping of air into the eye, it is necessary to provide vent passageway 86 extending through the cylindrical wall 52c and the inner support 68. The oscillation of the shaft 26a and accompanying flexure of the boot 58 tends to create pressure or vacuum surges within the handpiece 22, which surges are transmitted through tube 34 to the interior of the eye being operated upon. The passageways 86 vent the area adjacent the boot 58 to the outside atmosphere and prevent any such surges.

Figure 12:
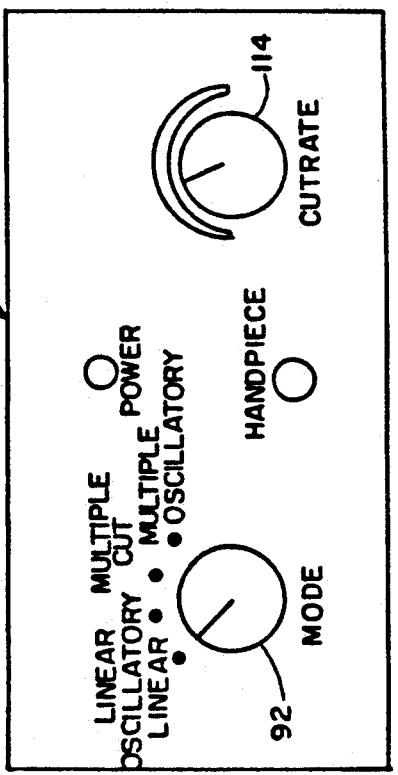
FIG. 12 is a showing of the control means for the scissors embodying the invention.
Figure 13:
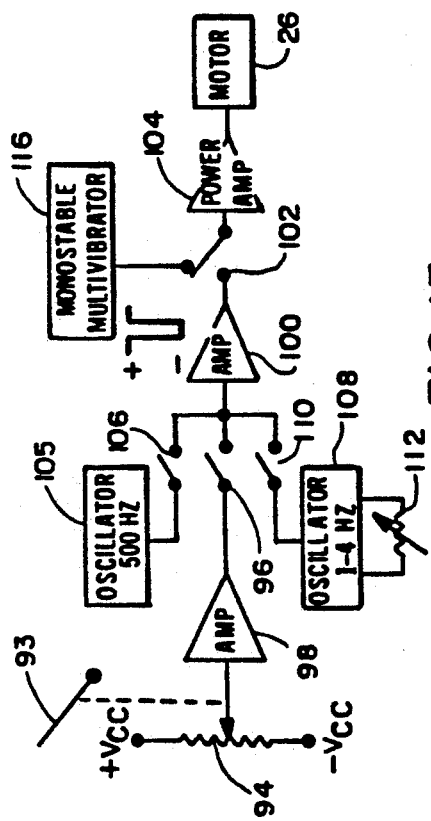
FIG. 13 is a schematic circuit diagram of the motor control circuit for the scissors embodying the invention.
Figure 21:
FIGS. 21 to 26 are photomicrographs of tissue from the corneas of chickens showing the results of sectioning this tissue with prior art intraocular scissors.
Figure 22:
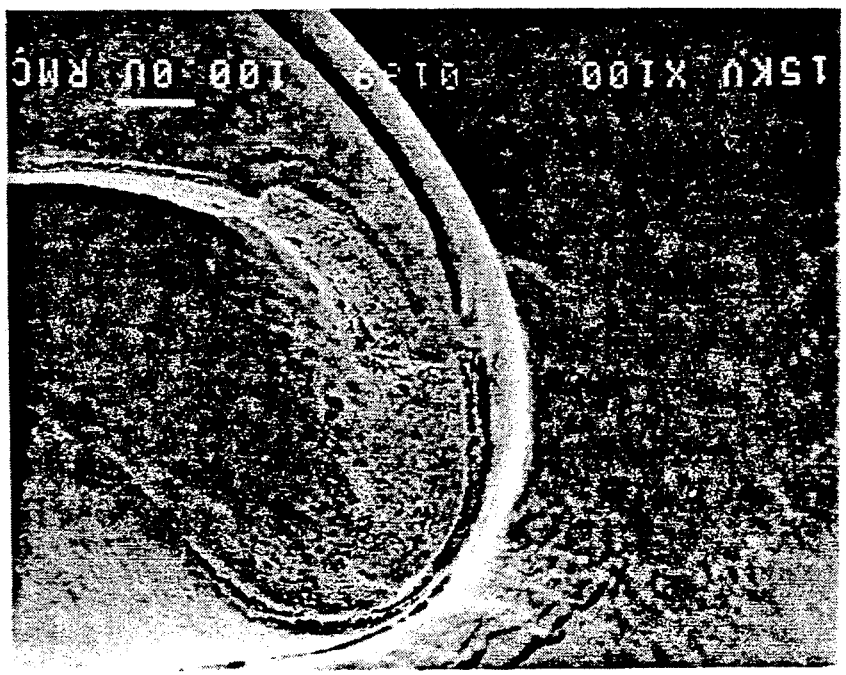
Figure 23:
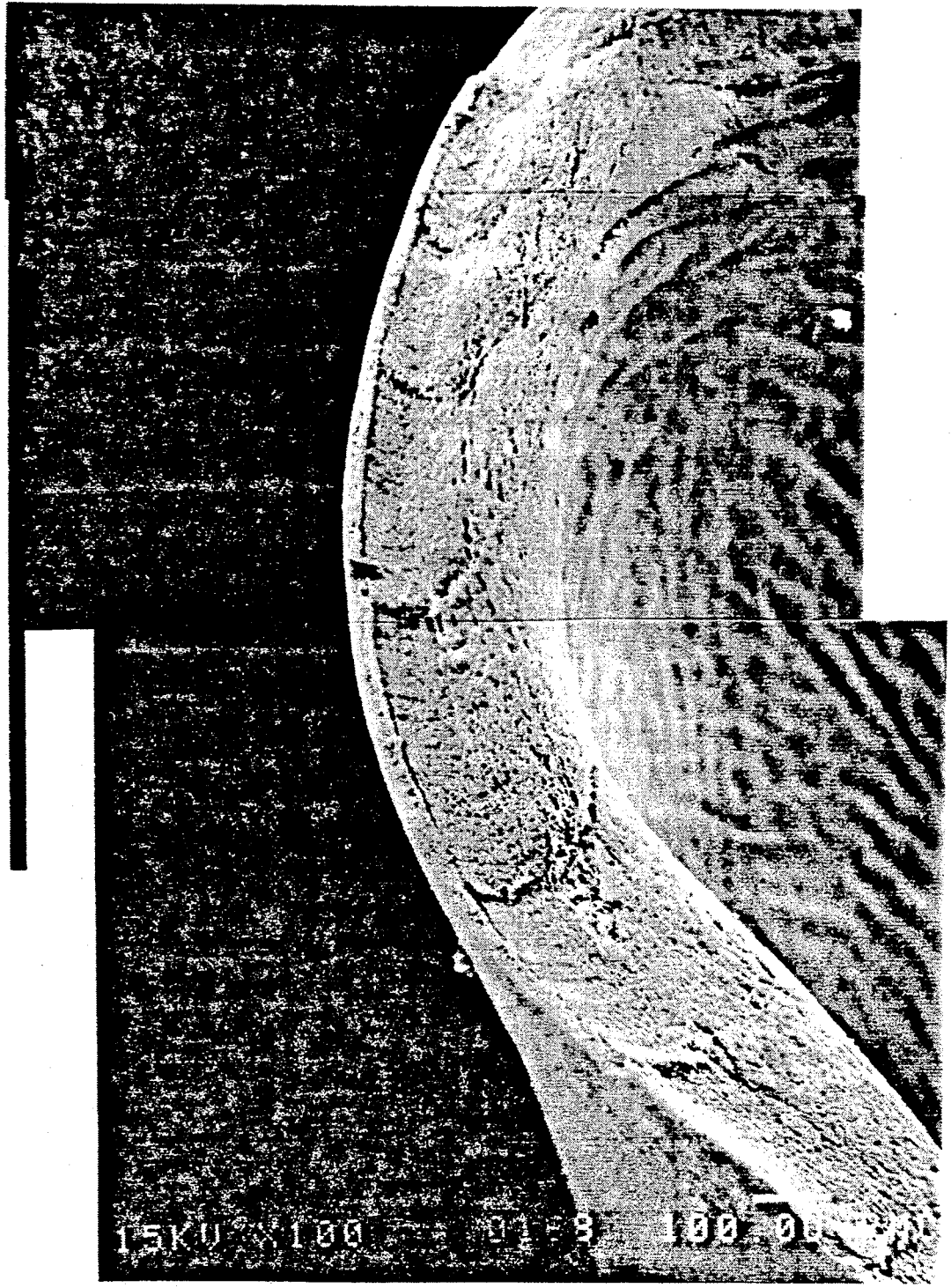
Figure 24:
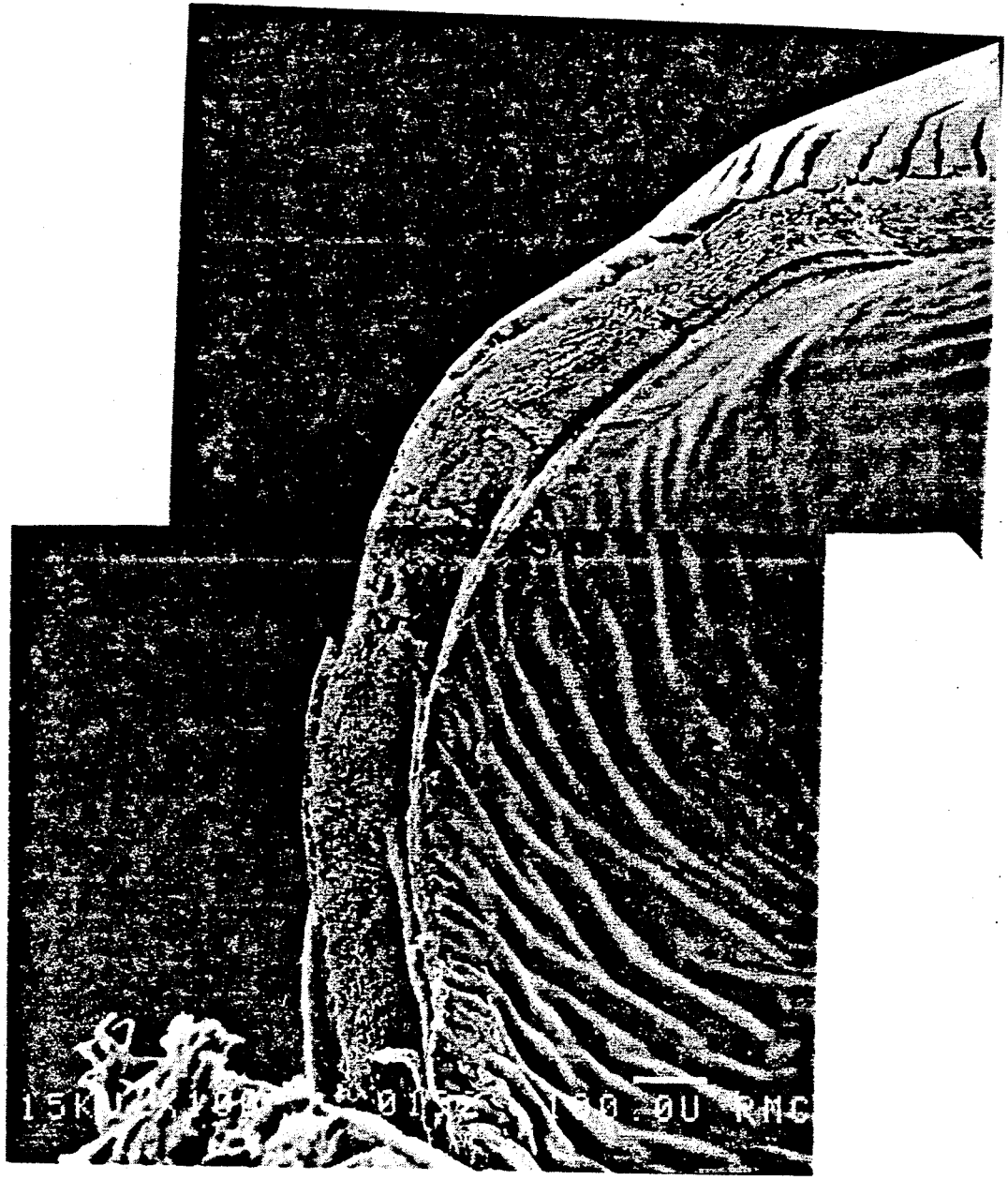
Figure 25:
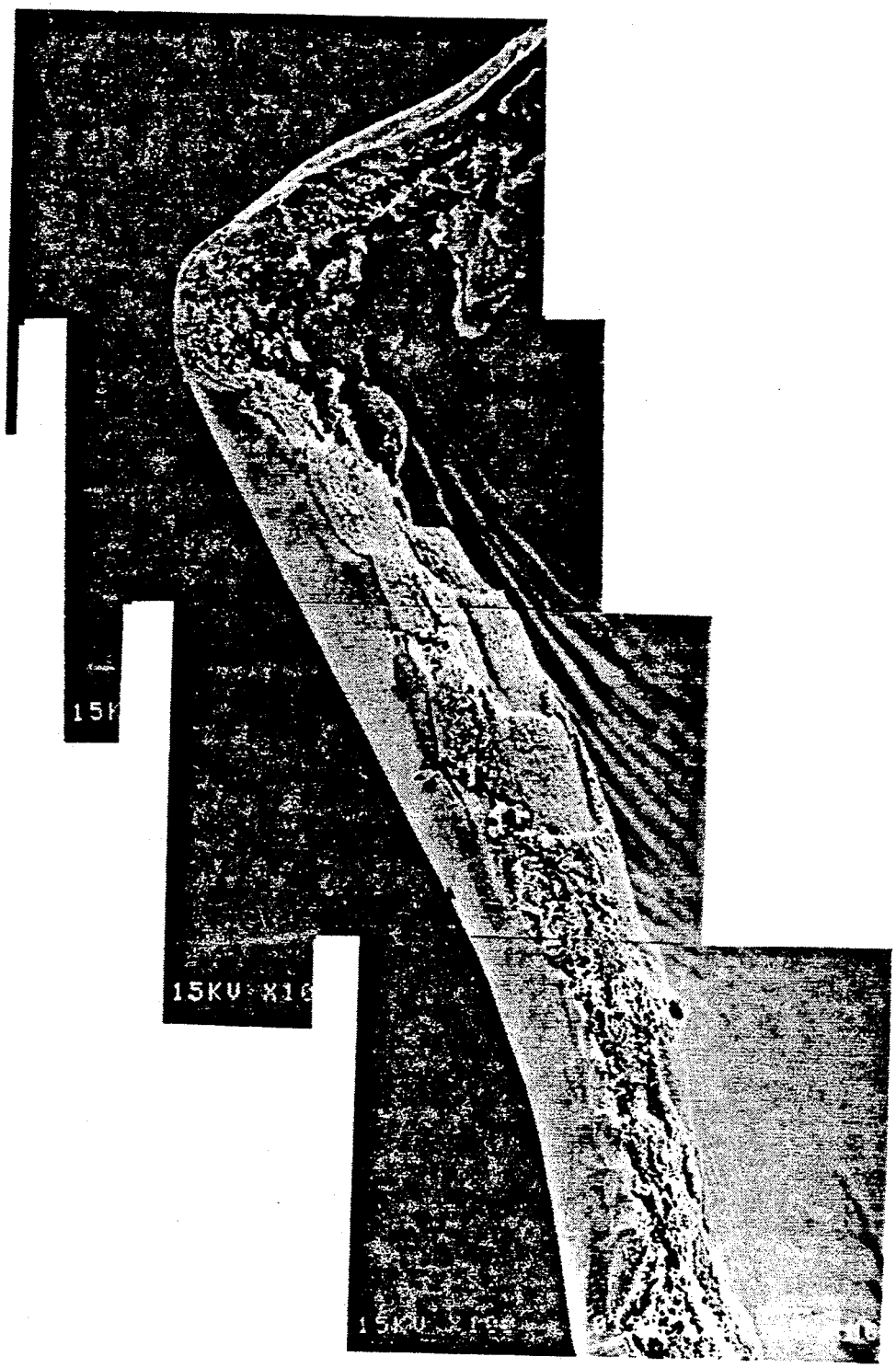
Figure 26:
Figure 27:
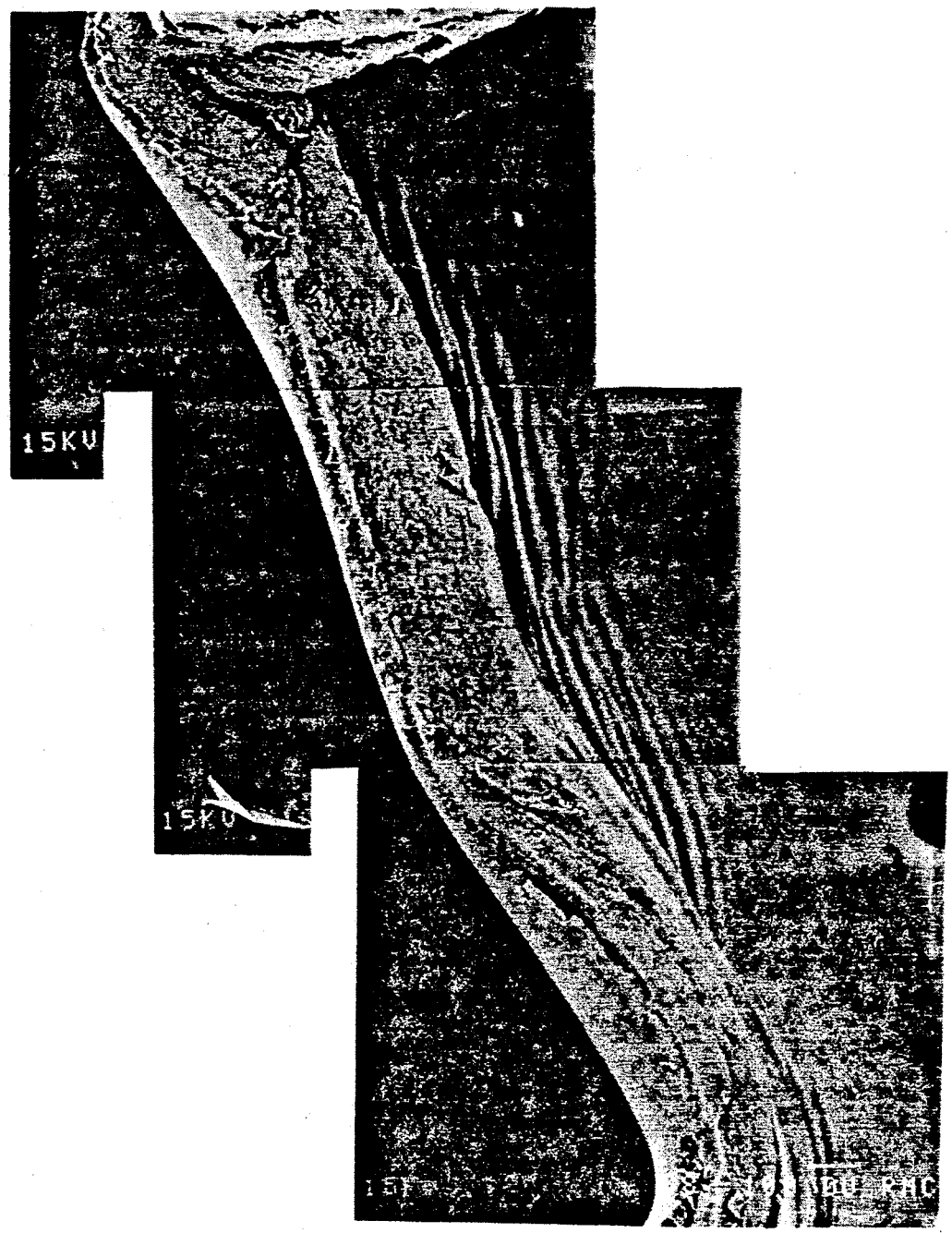
FIGS. 27 and 28 are photomicrographs of such chicken cornea tissue showing the results of sectioning this tissue with the scissors of the present invention.
Figure 28:
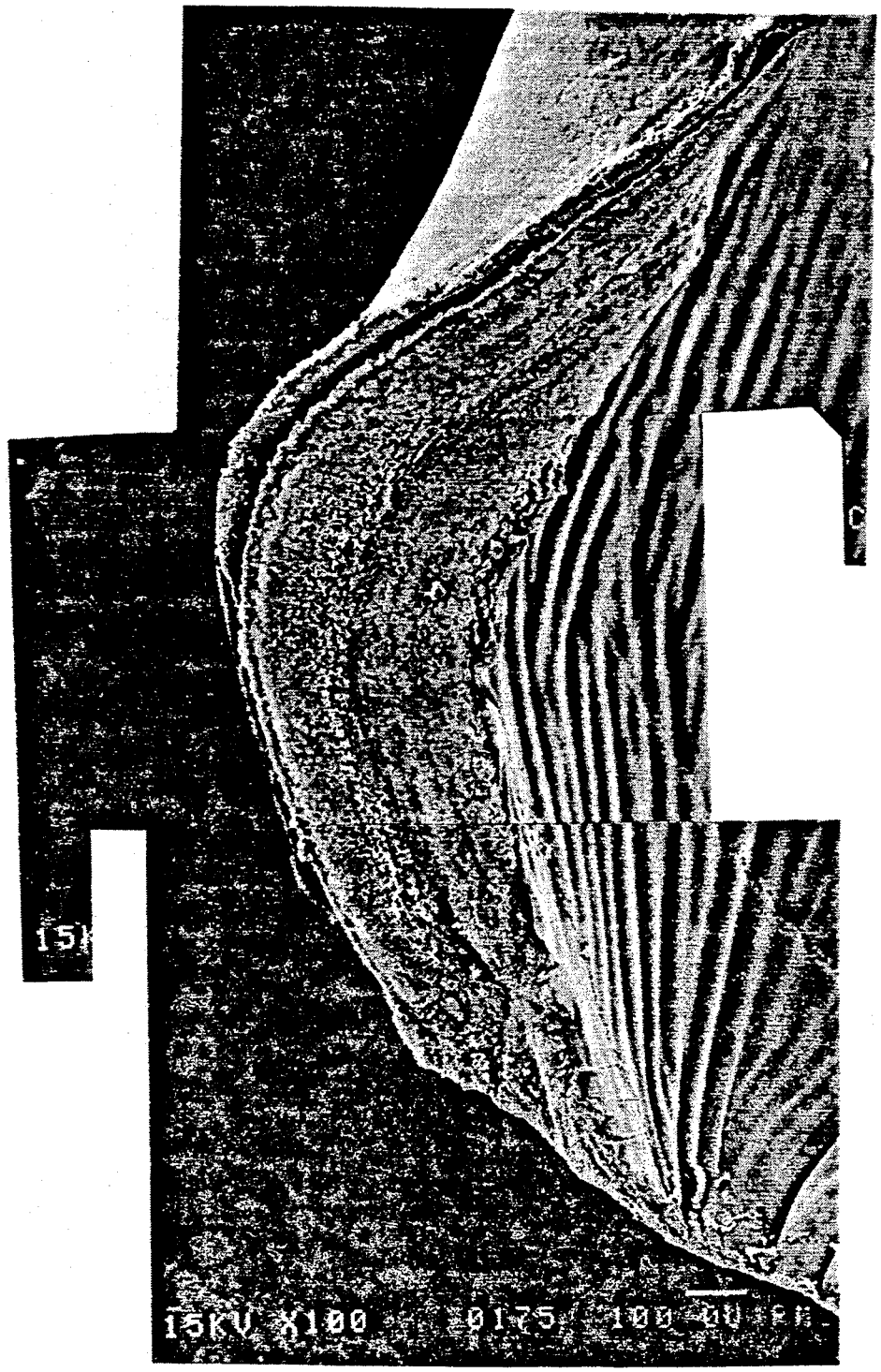

Turning now to the various modes in which the scissors 22 may be operated, attention is directed to the control as shown in FIG. 12 and the circuit diagram of FIG. 13. As shown in FIG. 12, there is provided a control means designated generally by reference numeral 90. The control means 90 includes a mode selection means 92 which permits the operator to select between four different modes of operation. The first mode is a so-called "linear mode" in which a current is applied to the field coils 26f of the motor 26, to achieve a desired displacement of the armature shaft 26a and thereby, a specific displacement of the movable blade member 30 with respect to the fixed blade member 28. This total displacement or excursion of the movable blade is on the order of 50 to 70 mils (0.050 to 0.070 inch). The control of the blade position in the linear setting is accomplished by a foot pedal 93 which operates a potentiometer 94, to deliver a selected DC voltage to the motor 26. As shown in the circuit diagram of FIG. 13, in the linear mode setting for the mode selection means 92, a first switch 96 is closed to deliver a voltage amplified by amplifier 98 through a summing amplifier 100, through a switch 102, amplifier 104, to the motor 26. The switch 102 is associated with the foot pedal control 93 and is a double pole switch for foot pedal 93 which is shown in FIG. 13 in its off position. Switch 102 is closed upon the initial operation of the foot pedal to connect the DC signal from potentiometer 94 in the case of the linear operation, to the motor 26.

As discussed earlier, the linear mode permits the operator to open and close the blades 28b and 30b to make individual cuts as the foot pedal 93 is depressed. This mode also permits the operator to select a desired spacing of the blades for any desired procedure.

In the second position of the mode selection means 92, designated as "linear oscillatory", the position of the movable blade is again controlled in a linear fashion by the position of the foot pedal which adjusts the potentiometer 94. In the linear oscillatory mode, the switch 96 is still closed, but the control also connects in circuit an oscillator 105 by closing a switch 106, thereby connecting the oscillator 105 as well as the potentiometer 94 to the summing amplifier 100. The summing amplifier 100 combines the DC signal and high-frequency oscillation signal and delivers it through the switch 102 and the power amplifier 104 to the motor 26. In this mode, with this circuit arrangement the scissors 20 may be operated in a particularly advantageous mode for many types of surgical procedures. The movable blade 30a may be positioned by the foot pedal operation of the potentiometer 94 to any desired degree of separation from the stationary blade 28b. At the same time, the high-frequency oscillator 105 causes the armature of the motor 26 to vibrate at a rate of 500 Hz through a relatively small displacement. This small displacement vibration, which may be from 0.001 to 0.003 inches, produces an effect on cutting of certain types of tissue which allows the blade to move easily through the tissue, cutting with a minimum amount of distortion or displacement of the tissue.

As discussed above, the high frequency vibratory motion in combination with the partially opened blades provides significant advantages in having the vibratory motion to cut tissues while maintaining an optimum position of the cutting point or intersection of the cutting edges. Under this condition, there is a small outward thrust against the tissue which is gathered and fed into the cutting point by the diverging cutting edges. The operator may move the blades forwardly with the blades spaced as in FIG. 11b, to cut tissue along a flat plane with little or no tissue deformation and may easily change the direction of cutting, since the tips of the blades are not buried in the tissue being cut.

The third setting provided on the mode selection means 92 is for a multiple cut. In the multiple cut setting of the control means 92, an oscillator 108 is connected through a switch 110 to the amplifier 100, as shown in FIG. 13. The oscillator 108 includes control means 112, so that the output frequency of the oscillator 108 may be varied between 1 and 4 Hz, or between 60 and 240 oscillations per minute. The control means 112 for the oscillator 108 may be adjusted by a control knob 114 on the control 90, as shown in FIG. 12. In the multiple-cut mode, the movable blade 30b reciprocates at a selected frequency with respect to the stationary blade 28. As discussed above, the contour of the cutting edges 30d and 28c of the movable and stationary blades provides improved cutting of delicate tissue in any of the modes of operation described. The diverging angle of the cutting edges allows the tissue to be gathered in as the instrument moves forward, and the acute angle of engagement of the two cutting edges reduces the outward thrust on the tissue being cut.

The fourth possible mode of operation for the scissors 20 is the multiple-oscillatory mode, and is indicated as the most clockwise setting for the mode selection means 92. At the multiple-oscillatory setting, the two switches 106 and 110 are both closed, connecting the oscillators 105 and 108 to the summing amplifier 100, through the switch 102 and the power amplifier 104 to the motor 26. In this particular mode of operation, the two oscillator signals are combined together to open and close the scissors periodically at a frequency of from 1 to 4 Hz, and at the same time cause the moving blade to vibrate at a high frequency. To best appreciate the nature of the signal applied to the motor 26, attention is directed to FIG. 14 which is a diagram of the voltage or current signal applied to the motor 26. The first two square waves represent the output of the oscillator 108 as amplified and fed to the motor 26, as would exist in the normal multiple-cut setting of the control means 92. With the control means set for the multiple-oscillatory mode, the oscillator 105 would be providing a signal superimposed on the signal from the oscillator 108. Thus, the square wave from oscillator 108 might be at a 2 Hz frequency, whereas the oscillator 105 would be producing a 500 Hz signal which would be superimposed on the signal from the oscillator 108. The result is that the movable blade continually vibrates as it is moved from one position to another. While FIG. 14 shows the applied signal, it should be appreciated that the inertia of the system results in the movable blade not moving immediately between one position and the other, since this movement would be slowed by the necessity to accelerate the blade, the coupling, the armature shaft, etc. As a consequence, the results obtained from applying a signal of this nature is a constant vibration of the movable blade as it moves from the various positions in opening and closing.

As indicated above, the switch 102 is closed at the time the food pedal is operated to move the potentiometer to a desired position. When the foot pedal is released, the switch 102 is activated to the position shown in FIG. 13, causing a mono-stable multi-vibrator 116 to deliver a short negative pulse to the power amplifier 104 and the motor 26. The purpose of this negative pulse is to cause the movable blade to be displaced to an open position at the end of the surgical procedure and thereafter be returned to the closed position by the positive DC signal.

The specific embodiment disclosed includes a detachable assembly having relatively reciprocable scissors blades. It is contemplated that the handpiece 22 would be used as a driver for a single blade instrument such as a knife or scalpel, or for a pair of surgical forceps. The handpiece 22 would drive the blade in the vibration mode to provide improved cutting action. In connection with the forceps, it is often necessary in ocular surgery to separate layers of tissue using forceps. It has been found that by vibrating the forceps, the task of separating such layers of tissue is facilitated considerably.

It is also contemplated that the scissors 20 and the handpiece 22 may be used for vitrectomy and fragmentation. The handpiece is a suitable source of power for the well-known vitrectomy instruments having cylindrical cutters in a hollow needle with suction means for withdrawing the cut tissue. For fragmentation of cataracts, the handpiece 22 may be used to drive a cylindrical aspirating tube at a high frequency of 500 to 800 Hz.

It is noted that the form of the ocular scissors may be varied within the scope of the present invention and those various scissors may be used with a handpiece in the various modes of operation discussed above. Thus, a scissors having blades oscillating in a plane perpendicular to the axis of the tube or needle may be mounted on a handpiece and driven in the four various vibrating and oscillating modes disclosed above.

While the disclosed embodiment of the ocular scissors is intended primarily for retinal surgery at the back of the eye, it is contemplated that the invention is suitable for cornea or lens surgery at the front of the eye. The only adaptation or difference between the instruments suitable for these different areas of surgery relates to the amount of movement of the movable blade, since the depths of cut required in cornea surgery is considerably greater than in retina surgery.

What is claimed is:

1. An intraocular scissor system for cutting tissue of an eye comprising:
    a handle body for gripping by a surgeon during a cutting operation;
    a pair of blades extending from the body with at least one of the blades being movable relative to the other blade between a fully open position and a fully closed position;
    a tubular needle extending from the handle body and having the movable blade movable therein;
    a driver means in the handle body for operating at least one of said blades in a vibratory mode with a small, predetermined amplitude and a high, predetermined frequency less than an ultrasonic frequency, the driver driving the said scissor blades to superimpose the vibratory mode on an oscillating mode in which at least one movable blade is operated through an amplitude substantially greater than the small predetermined amplitude and at a lower frequency than the high predetermined frequency to open and close the scissors while the blades moving through the small amplitude vibrate the tissue to sever tissue in the vibratory mode as the movable blade oscillates.

2. An intraocular scissor system in accordance with claim 1 in which the driver comprises an electrical solenoid; and a D.C. current drives the solenoid to oscillate the movable blade and an A.C. current is superimposed on the D.C. current to drive the solenoid to vibrate the movable blade.

3. An intraocular scissor system in accordance with claim 2 in which the oscillating frequency is in the range of 1 to 5 cycles per second, and in which the vibratory frequency is in excess of 200 cycles per second.

4. An intraocular scissor system in accordance with claim 2 including a manual operating means to shift the blades to a closed position when the power fails to allow removal of the scissor blades from the eye in a closed position if the power should fail.

5. An intraocular scissor system in accordance with claim 4 in which one of the blades is normally a stationary blade; and in which the manual operator shifts the normal stationary blade to a closed position next to the movable blade.

6. An intraocular scissor system in accordance with claim 1 including a foot pedal to shift the scissor blades to a partially open position and to the open and closed positions.

7. An intraocular scissor system in accordance with claim 5 including a control means which controls the driver for operating in the vibratory mode only, the oscillatory mode only, and a linear mode in which an operation of the foot pedal causes a single closing and opening movement of the movable blade, and a multiple mode having both the linear and vibratory modes simultaneously.

8. An intraocular scissor system in accordance with claim 1 in which the pair of blades and the tubular needle are detachably mounted to the handle body, and a coupling means is affixed to the tubular needle and blades to releasably couple the tubular needle and blades to the handle body.

9. An intraocular scissor system in accordance with claim 1 in which the movable blade reciprocates in a first direction and has a cutting edge extending laterally relative to the first direction, the other blade extending parallel to the movable blade and having a cutting edge extending laterally to the first direction, the cutting edges of the movable and fixed blades defining an opening therebetween converging to a contact point, the converging cutting edges funnelling tissue to the vibratory contact point.

10. An intraocular scissor system in accordance with claim 1 including a detachable assembly carrying the blades for detachment from the handle body for steam autoclaving, the driver including a linear electric motor in the handle body, and seals in the handle body for sealing the electric linear motor against intrusion of steam when the handle body is steam autoclaved.

11. An intraocular scissor system in accordance with claim 10 in which the handle body has a stationary part and the linear motor has a movable member, the seals comprise a flexible boot secured at one end to the stationary part of the handle body and secured at another end of the boot to the movable member of the linear motor connected to reciprocate the movable blade.

12. An intraocular scissor system in accordance with claim 1 in which the handle body is tubular in shape and fits between the thumb and forefinger of a surgeon, the tubular body being rotatable between the surgeon's thumb and forefinger to change the direction of cutting.

13. A microsurgical, intraocular instrument for eye surgery comprising:
   a handle body for gripping with one hand by a surgeon during surgery;
   a surgical tool having a movable blade projecting from the handle body and having a member adapted to be vibrated at a frequency above the natural frequency of vibration of the tissue in the eye;
   an adapter for detachably connecting each of a plurality of surgical tools to the handle body for reciprocal movement during the surgery, the adapter and surgical tools being steam autoclavable;
   an electric linear motor in the handle body having an armature for vibrating the surgical tool at a frequency in excess of 200 cycles per second and less than an ultrasonic frequency and for operating the surgical tool in a linear mode in which the movable blade of the surgical tool is located at an intermediate position between a fully opened and a fully closed position while the movable blade is vibrating; and
   means for sealing the electric linear motor and armature in the handle body to allow autoclaving of the handle body with the linear motor therein between attachments of different surgical tools.

14. A microsurgical, intraocular instrument in accordance with claim 13 in which the surgical tool is a scissors.

15. A microsurgical, intraocular instrument in accordance with claim 13 in which a suction tube is connected to the hollow body and through the surgical tool for vitreous applications.

16. A microsurgical, intraocular scissor system for operating in an eye comprising:
   a tubular handle body for gripping by the surgeon with one hand during surgery;
   a fixed tubular needle projecting from the handle body for insertion through a slit into the eye;
   a pair of blades extending from an end of the tubular needle with the blades being movable relative to one another between a closed position and an open position through a first large amplitude; and
   a driver motor in the tubular handle body for operating in multiple-oscillating mode with the blades oscillating a first frequency between open and closed positions and having superimposed thereon a series of vibratory cutting strokes each having an amplitude which is small fraction of the first large amplitude and at a frequency substantially above 200 cycles per second and less an ultrasonic frequency.

17. A microsurgical, intraocular scissor system in accordance with claim 16 in which the driver motor is an electric linear motor operable at a frequency less than 1,000 cycles per second.

18. A microsurgical, intraocular scissor system in accordance with claim 17 in which the linear motor is driven by a D.C. current to oscillate the scissors through the first large amplitude between the fully open and the fully closed positions, at a lower frequency, an A.C. current superimposed on the D.C. current motor current to drive the movable scissor blade at the high frequency through the very small amplitude as the movable blade is moving toward or from the fixed blade.

19. A microsurgical, intraocular scissor system in accordance with claim 16 including a vent hole in the tubular handle body to vent air to prevent air from being pushed by the driver through the tubular needle and into the eye.

20. A microsurgical, intraocular scissor system in accordance with claim 16 which includes a manual operable means to shift the blades to a closed position for removal through a slit in the eye if the power should fail.

21. A microsurgical, intraocular scissor system in accordance with claim 16 in which cutting edges on the blades define therebetween a converging shape from their outer edges to a point of contact therebetween to guide tissue to the point of contact, the movable blade being reciprocated in its direction of length with its cutting edge extending laterally from its direction of reciprocation.

22. A microsurgical scissors system for cutting tissue, such as tissue from an eye, comprising:
   a handle body for gripping by a surgeon during a tissue removal operation,
   a linear actuator in the body and having an armature which is movable axially with electrical activation of the armature,
   a microsurgical device having a pair of blades extending from the body with at least one of the being movable relative to the other blade between an open position and a closed position, and
   circuit driver means for operating the armature to move the pair of blades in each of four different modes of operation comprising:
   a) a linear mode in which the movable blade is movable between its open and closed positions;
   b) a multi-cut oscillating mode in which the movable blade oscillates between the open and closed positions at a predetermined low oscillating frequency;
   c) multiple-oscillating mode in which the movable blade is vibrating in a vibratory mode at a substantially higher frequency than the oscillating frequency while also oscillating in the multi-cut oscillating mode; and
   d) a linear oscillating mode in which the movable blade is in an intermediate position between a fully open and a fully closed position while the movable blade is vibrating.

* * * * *

UNITED STATES PATENT AND TRADEMARK OFFICE
CERTIFICATE OF CORRECTION

PATENT NO. : 5,275,607
DATED : January 4, 1994
INVENTOR(S) : Lo et al.

It is certified that error appears in the above-indentified patent and that said Letters Patent is hereby corrected as shown below:

On the cover page, Item [73], change Assignee from "Visionary Medical, Inc., Fremont, Calif." to -- Grieshaber & Co., A.G., Schaffhausen, Switzerland --.

Signed and Sealed this

Twenty-ninth Day of August, 1995

Attest:

BRUCE LEHMAN

*Attesting Officer*  *Commissioner of Patents and Trademarks*